United States Patent
Rong et al.

(10) Patent No.: US 9,488,645 B2
(45) Date of Patent: Nov. 8, 2016

(54) CELL-BASED MICROARRAYS AND METHODS OF USE

(76) Inventors: Jianhui Rong, Edmonton (CA); Kevin Paul Kane, Edmonton (CA)

( * ) Notice: Subject to any disclaimer, the term of this patent is extended or adjusted under 35 U.S.C. 154(b) by 2612 days.

(21) Appl. No.: 12/063,233

(22) PCT Filed: Sep. 9, 2005

(86) PCT No.: PCT/US2005/032392
§ 371 (c)(1),
(2), (4) Date: Mar. 26, 2009

(87) PCT Pub. No.: WO2007/032761
PCT Pub. Date: Mar. 22, 2007

(65) Prior Publication Data
US 2009/0215645 A1    Aug. 27, 2009

(51) Int. Cl.
*C40B 30/06* (2006.01)
*G01N 33/50* (2006.01)

(52) U.S. Cl.
CPC ............. *G01N 33/505* (2013.01); *C40B 30/06* (2013.01); *G01N 2333/96466* (2013.01)

(58) Field of Classification Search
None
See application file for complete search history.

(56) References Cited

U.S. PATENT DOCUMENTS

| 6,544,790 | B1 | 4/2003 | Sabatini et al. |
| 2001/0041347 | A1 | 11/2001 | Sammak et al. |
| 2002/0006664 | A1 | 1/2002 | Sabatini et al. |
| 2003/0124613 | A1 | 7/2003 | Hildebrand et al. |
| 2003/0203486 | A1 | 10/2003 | Sabatini |
| 2003/0211548 | A1 | 11/2003 | Packard et al. |
| 2003/0228601 | A1 | 12/2003 | Sabatini |
| 2003/0228694 | A1 | 12/2003 | Sabatini |
| 2005/0019843 | A1 | 1/2005 | Chen et al. |

OTHER PUBLICATIONS van den Bruggen et al. (Dec. 13, 1991) Science vol. 254 p. 1643 to 1647.*
Amstad, P.A., et al. Detection of caspase activation in situ by fluorochrome-labeled caspase inhibitors. Bio Techniques. 2001, vol. 31, No. 3, pp. 608-610, 612,614, passim.
Boon, T., et al. Human tumor antigens recognized by T lymphocytes. The Journal of Experimental Medicine. 1996, vol. 183, No. 3, pp. 725-729.
Greenfield, A., et al. An H-YDb epitope is encoded by a novel mouse Y chromosome gene. Nature Genetics. 1996, vol. 14, No. 4, pp. 474-478.
Guerder, S., et al. B7 costimulation is necessary for the activation of the lytic function in cytotoxic T lymphocyte precursors. Journal of Immunology. 1995, vol. 155, No. 11, pp. 5167-5174.
Pardoll, D. Does the immune system see tumors as foreign or self? Annual Review of Immunology. 2003, vol. 21, pp. 807-839. Epub Dec. 19, 2001.

(Continued)

*Primary Examiner* — Christian Boesen
(74) *Attorney, Agent, or Firm* — Carol Francis; Bozicevic, Field & Francis LLP

(57) ABSTRACT

The invention provides methods and compositions for rapid, sensitive, and highly specific detection of antigen-specific interactions between cytolytic T lymphocytes (CTLs) and antigen presenting cells (APCs). The invention also features compositions, including kits, for use in the methods of the invention.

13 Claims, 3 Drawing Sheets

(56) References Cited

OTHER PUBLICATIONS

Rong, J., et al. TG3.1.2 Prostate Cancer CTL Antigens. PowerPoint slides presented at The Society for Biomolecular Screening (SBS) 10$^{th}$ Anniversary Conference and Exhibition, Sep. 11-15, 2004, Gaylord Palms Resort and Convention Center, Orlando, Florida.

Soen, Y., et al. Detection and characterization of cellular immune responses using peptide-MHC microarrays. PLoS Biology. 2003, vol. 1, No. 3, pp. 429-438. Epub Dec. 22, 2003.

Stone, J.D., et al. HLA-restricted epitope identification and detection of functional T cell responses by using MHC-peptide and costimulatory microarrays. Proc Natl Acad Sci USA. 2005, vol. 102, No. 10, pp. 3744-3749. Epub Feb. 23, 2005.

Van Den Eynde, B., et al. The gene coding for a major tumor rejection antigen of tumor P815 is identical to the normal gene of syngeneic DBA/2 mice. The Journal of Experimental Medicine. 1991, vol. 173, No. 6, pp. 1373-1384.

Van Der Bruggen, P., et al. Tumor-specific shared antigenic peptides recognized by human T cells. Immunological Reviews. 2002, vol. 188, pp. 51-64.

Wong, P., et al. CD8 T cell responses to infectious pathogens. Annual Review of Immunology. 2003, vol. 21, pp. 29-70. Epub Dec. 19, 2001.

Yewdell, J.W., et al. Understanding presentation of viral antigens to CD8+ T cells in vivo: the key to rational vaccine design. Annual Review of Immunology. 2005, vol. 23, pp. 651-682.

Ziauddin, J., et al. Microarrays of cells expressing defined cDNAs. Nature. 2001, vol. 41•1, pp. 107-110.

Cortesini et al. Distinct mRNA Microarray Profiles of Tolerogenic Dendritic Cells. Human Immunology 62, 1065-1072 (2001).

Liu et al. Visualization and Quantification of T Cell-Mediated Cytotoxicity Using Cell-Permeable Fluorogenic Caspase Substrates. Nature Med. 8(2) 185-189 (2002).

BIOMOL Carboxyfluorescien Multi-Caspase Activity Kit Apoptosis Detection AK-117. Product Insert, BIOMOL® Research Laboratories, Inc. 2002.

Barry, M., et al. Cytotoxic T lymphocytes: All roads lead to death. Nature Reviews. Jun. 2002, vol. 2, pp. 401-409.

Wu, R., et al. Cell-biological applications of transfected-cell microarrays. Trends in Cell Biology. Oct. 2002, vol. 12, No. 10, oo. 485-488. Epub: Sep. 3, 2002.

Martz, 1975, "Early Steps in Specific Tumor Cell Lysis by Sensitized Mouse T Lymphocytes: I. Resolution and Characterization" J. Immunol., 115:261-267.

Zagury et al., 1975, "Isolation and characterization of individual functionally reactive cytotoxic T lymphocytes: conjugation, killing and recycling at the single cell level" Eur. J. Immunol., 5:818-822.

Abrams et al., 1989, "Cytotoxic T Lymphocyte-induced Loss of Target Cell Adhesion and Lysis Involve Common and Separate Signaling Pathways" J. Immunol., 142:1789-1796.

Russell John H., et al. Loss of Adhesion a Novel and Distingct Effect of the Cytotoxic T Lymphocyte-Target Interaction. Journal of Immunologisis. 1988. 140(427-432).

Liu, L., et al. Assessment of lymphocyte-mediated cytotoxicity using flow cytometry. Methods in Molecular Biology: vol. 263, Flow Cytometry Protocols, Second Ed., Edited by T.S. Hawley and R.G. Hawley. 2004, Chapter 7, pp. 125-139, Humana Press, Totowa, NJ.

\* cited by examiner

SEQUENCE LISTING

```
<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: HY peptide Uty246-254

<400> SEQUENCE: 1

Met Trp Met His His Asn Met Asp Leu Ile
1               5                   10

<210> SEQ ID NO 2
<211> LENGTH: 36
<212> TYPE: DNA
<213> ORGANISM: Artificial Sequence
<220> FEATURE:
<223> OTHER INFORMATION: Sense HY peptide Uty246-254 Oligonucleotide

<400> SEQUENCE: 2
ggccgccatg tggatgcacc ataatatgga tctaat                                36
```

```
<210> SEQ ID NO 3
<211> LENGTH: 36
<212> TYPE: DNA
<213> ORGANISM: Artificial Sequence
<220> FEATURE:
<223> OTHER INFORMATION: Antisense HY peptide Uty246-254 Oligonucleotide

<400> SEQUENCE: 3
ctagattaga tccatattat ggtgcatcca catggc                                36

<210> SEQ ID NO 4
<211> LENGTH: 48
<212> TYPE: DNA
<213> ORGANISM: Artificial Sequence
<220> FEATURE:
<223> OTHER INFORMATION: Sense EGFP-HY Minigene Fusion Construct
      Oligonucleotide

<400> SEQUENCE: 4
gatcccaaca gttaggttgg atgcaccata atatggatct aatttgat                  48

<210> SEQ ID NO 5
<211> LENGTH: 48
<212> TYPE: DNA
<213> ORGANISM: Artificial Sequence
<220> FEATURE:
<223> OTHER INFORMATION: Antisense EGFP-HY Minigene Fusion Construct
      Oligonucleotide

<400> SEQUENCE: 5
ctagatcaaa ttagatccat attatggtgc atccaaccta actgttgg                  48

<210> SEQ ID NO 6
<211> LENGTH: 13
<212> TYPE: PRT
<213> ORGANISM: Artificial Sequence
<220> FEATURE:
<223> OTHER INFORMATION: HY Peptide Oligonucleotide

<400> SEQUENCE: 6

Gln Gln Leu Gly Trp Met His His Asn Met Asp Leu Ile
 1               5                  10

<210> SEQ ID NO 7
<211> LENGTH: 9
<212> TYPE: PRT
<213> ORGANISM: Artificial Sequence
<220> FEATURE:
<223> OTHER INFORMATION: HY Peptide Uty246-254 Oligonucleotide

<400> SEQUENCE: 7

Trp Met His His Asn Met Asp Leu Ile
 1               5
```

CELL-BASED MICROARRAYS AND METHODS OF USE

FIELD OF THE INVENTION

The invention generally relates to use of cell-based microarrays in the detection of cytotolytic T lymphocyte (CTL)-antigen recognition.

BACKGROUND OF THE INVENTION

The CD8+ T lymphocyte subset can play an important role in immunosurveillance against tumorigenesis and virus infection (Pardoll, D. *Annu. Rev. Immunol.* 21, 807-839 (2003); Wong, P. & Pamer, E. *Annu. Rev. Immunol.* 21, 29-70 (2003)). Peptides presented by major histocompatibility complex (MHC) class I molecules on diseased cells can be recognized by CD8+ T cells (Yewdell, J. W. & Haeryfar, S. M. *Annu. Rev. Immunol.* 23, 651-682. (2005)). Selectivity of CTL for antigen-expressing cells can be directed toward targeted mortality in anti-virus or cancer therapy, if antigens are known.

A key step in developing T cell therapies is therefore to identify CTL-recognized antigens selectively expressed by a desired target cell, such as a tumor cell or virus infected cell. Typically, identification of such antigens has involved screening cDNA libraries as cDNA pools through a lengthy multi-step process in multi-well plates (Van den Eynde, B. Lethe, B., Van Pel, A., De Plaen, E. & Boon, T. *J. Exp. Med.* 173, 1373-1384 (1991); Boon, T. & van der Bruggen, P. *J. Exp. Med.* 183, 725-729 (1996); Van der Bruggen, P. et al. *Immunol. Rev.* 188, 51-64 (2002). Antigen-specific CTLs detect the presence of antigen-encoding DNA sequences in each cDNA pool. Hundreds of genes in individual cDNA pools compete for expression in antigen presenting cells (APC), causing difficulty in identifying rarely expressed antigens. In addition, low throughput in assessment of CTL cytotoxicity using current methods hampers antigen identification.

Although microarrays have been used successfully to examine gene expression profiles on a genome-wide scale, exploitation of microarrays for cell-based functional screens is yet to be fully realized. Previously, T cell responses to recombinant MHC molecules bound with defined peptide antigens spotted on microarrays have been demonstrated (Soen et al. *PLoS Biology* 1, E65 (2003); Stone et al. *Proc. Natl. Acad. Sci. USA* 102, 3744-3749 (2005)). Such approaches are useful in detecting the presence of T cells that recognize a known antigen. Although random peptide libraries could be screened in an MHC protein array as an approach to identify novel T cell antigens, such a screen would not be able to detect antigens generated by natural processing events in live APC and identify their encoding cDNAs.

There is a need in the field for methods for sensitive and rapid identification of CTL antigens. The present invention addresses this need.

LITERATURE

Literature of interest includes:
US 2002/0006664; US 2003/0228694; US 2003/0228601; US 2003/0203486; and U.S. Pat. No. 6,544,790; US 2003/0211548; US 2005/0019843; US 2001/0041347.

Liu et al. *Nat. Med.* 8(2):185-189 (2002); Pardoll, D. *Annu. Rev. Immunol.* 21, 807-839 (2003); Wong, P. & Pamer, E. *Annu. Rev. Immunol.* 21, 29-70 (2003); Yewdell, J. W. & Haeryfar, S. M. *Annu. Rev. Immunol.* 23, 651-682. (2005); Barry, M. & Bleackley, R. C. *Nat. Rev. Immunol.* 2, 401-409 (2002); Van den Eynde et al. T. *J. Exp. Med.* 173, 1373-1384 (1991); Boon et al. *J. Exp. Med.* 183, 725-729 (1996); Van der Bruggen, P et al. *Immunol. Rev.* 188, 51-64 (2002); Ziauddin et al. *Nature* 411, 107-110 (2001); Wu et al. *Trends Cell. Biol.* 12, 485-488 (2002); Liu et al. *Methods Mol. Biol.* 263, 125-140 (2004); Amstad et al. *Biotechniques* 31, 608-610, 612, 614, passim (2001); Guerder et al. *J. Immunol.* 155, 5167-5174 (1995); Greenfield, A. et al. *Nat. Genet.* 14, 474-478 (1996); Soen et al. *PLoS Biology* 1, E65 (2003); Stone et al. *Proc. Natl. Acad. Sci. USA* 102, 3744-3749 (2005).

SUMMARY OF THE INVENTION

The invention provides methods and compositions for rapid, sensitive, and highly specific detection of antigen-specific interactions between cytolytic T lymphocytes (CTLs) and antigen presenting cells (APCs). The invention also features compositions, including kits, for use in the methods of the invention.

An advantage of the invention is that it provides a highly sensitive, specific method for detection of cytotolytic T lymphocyte (CTL)-antigen recognition. Using the methods of the invention, detection of CTL-mediated killing, which is indicative of a specific interaction between a CTL and an antigen-presenting cell (APC), at the single-cell level, e.g., at the level of a single interaction between a single CTL and a single APC present on the array. The invention is also advantageous in this regard as it requires very little starting material, e.g., with respect to the number of reactive CTLs that need to be in the sample for detection.

In one aspect, the invention features methods for identifying a CTL antigen, comprising contacting a sample comprising a CTL with an array comprising a plurality of recombinant antigen-presenting cells (APCs), where recombinant APCs expressing different, known target polynucleotides are provided at different, discrete locations on the array; and detecting the presence or absence of caspase activity in said recombinant APCs by detecting the presence of a fluorescent signal generated from a fluorogenic caspase substrate present in said recombinant APCs, where the presence of a fluorescent signal in a recombinant APC is indicative of an antigen-specific interaction between the CTL and the recombinant APC and indicates the recombinant APC contains a target polynucleotide encoding an antigen specifically recognized by the CTL.

In embodiments related to this aspect, the target polynucleotides encode a tumor antigen, and antigen of an intracellular pathogen, or an autoantigen. Where the antigen is an antigen of an intracellular pathogen, the antigen can be a viral antigen, bacterial antigen, antigen of a parasite, or fungal antigen. In further related embodiments, the fluorogenic caspase substrate is a fluorogenic multi-caspase substrate. In still further related embodiments, the CTL is in a biological sample obtained from a subject, or is a clone of a naturally-occurring CTL.

In another aspect, the invention features a method for detecting a CTL having an antigen specificity indicative of the presence of, or prior exposure of, a subject to a disease, where the method comprises contacting a biological sample comprising CTLs from a subject with an array comprising a plurality of recombinant APCs, where recombinant APCs expressing different, known target polynucleotides are provided at different, discrete locations on the array, and wherein the target polynucleotides encode a disease antigen;

and detecting the presence or absence of caspase activity in said recombinant APCs by detecting the presence of a fluorescent signal generated from a fluorogenic caspase substrate present in said recombinant APCs. The presence of a fluorescent signal in a recombinant APC is indicative of an antigen-specific CTL-recombinant APC interaction, and indicates the biological sample contains a CTL that specifically recognizes the disease antigen, indicating the subject has or previously had the disease for which the disease antigen is specific.

In embodiments related to this aspect, the target polynucleotides encode a tumor antigen, and antigen of an intracellular pathogen, or an autoantigen. Where the antigen is an antigen of an intracellular pathogen, the antigen can be a viral antigen, bacterial antigen, antigen of a parasite, or fungal antigen. In further related embodiments, the fluorogenic caspase substrate is a fluorogenic multi-caspase substrate. In still further related embodiments, the CTL is in a biological sample obtained from a subject, or is a clone of a naturally-occurring CTL.

In still another aspect, the invention features methods of screening a candidate CTL antigen, comprising contacting a cytotoxic T lymphocyte (CTL) with an array surface comprising multiple distinct regions comprising target antigen presenting cells (APCs), wherein the target APCs express different candidate CTL antigens encoded by different recombinant target polynucleotides, wherein the polynucleotides are introduced into APCs by plating APCs onto the array surface comprising the polynucleotide under appropriate conditions for introduction of the polynucleotide into the APC, such that an array location in which the polynucleotide was deposited corresponds to the location of the target APC expressing the polynucleotide; and detecting the presence or absence of CTL-mediated induction of apoptosis in the target APCs by detecting a detectable signal from a fluorogenic caspase substrate, wherein generation of a detectable signal from a fluorogenic caspase substrate is indicative of an increase in caspase activation, where detection of caspase activation in a target APC indicates the target APC expression a CTL antigen.

In embodiments related to this aspect, the target polynucleotides encode a tumor antigen, and antigen of an intracellular pathogen, or an autoantigen. Where the antigen is an antigen of an intracellular pathogen, the antigen can be a viral antigen, bacterial antigen, antigen of a parasite, or fungal antigen. In further related embodiments, the fluorogenic caspase substrate is a fluorogenic multi-caspase substrate. In still further related embodiments, the CTL is in a biological sample obtained from a subject, or is a clone of a naturally-occurring CTL.

In another aspect, the invention features, a method of screening a candidate agent for activity in modulating antigen-specific interaction between a CTL and an APC, contacting a candidate agent and a CTL with an array comprising a plurality of recombinant antigen-presenting cells (APCs), wherein recombinant APCs expressing different, known target polynucleotides are provided at different, discrete locations on the array, and wherein the target polynucleotides encode a target antigen of interest; and detecting the presence or absence of caspase activity in said recombinant APCs by detecting the presence of a fluorescent signal generated from a fluorogenic caspase substrate present in said recombinant APCs. An increase or decrease in a fluorescent signal in a recombinant APC relative to a fluorescent signal produced by CTL-APC interactions in the absence of the candidate agent indicates the candidate agent modulates antigen-specific CTL-APC interaction.

In embodiments related to this aspect, the target polynucleotides encode a tumor antigen, and antigen of an intracellular pathogen, or an autoantigen. Where the antigen is an antigen of an intracellular pathogen, the antigen can be a viral antigen, bacterial antigen, antigen of a parasite, or fungal antigen. In further related embodiments, the fluorogenic caspase substrate is a fluorogenic multi-caspase substrate. In still further related embodiments, the CTL is in a biological sample obtained from a subject, or is a clone of a naturally-occurring CTL.

The present invention can be developed into assays or manufactured into kits to be used in clinical laboratories or hospitals, e.g., for diagnosis of a disease (e.g., cancer, infectious disease, autoimmune disease, and the like). The assay can also be utilized in the development and clinical trials of vaccines and therapeutic drugs for treating diseases (e.g., cancer, infectious disease, autoimmune disease, and the like).

These and other advantages, aspects, and embodiments will be readily apparent to the ordinarily skilled artisan upon reading the present specification.

Definitions

Figure 1:
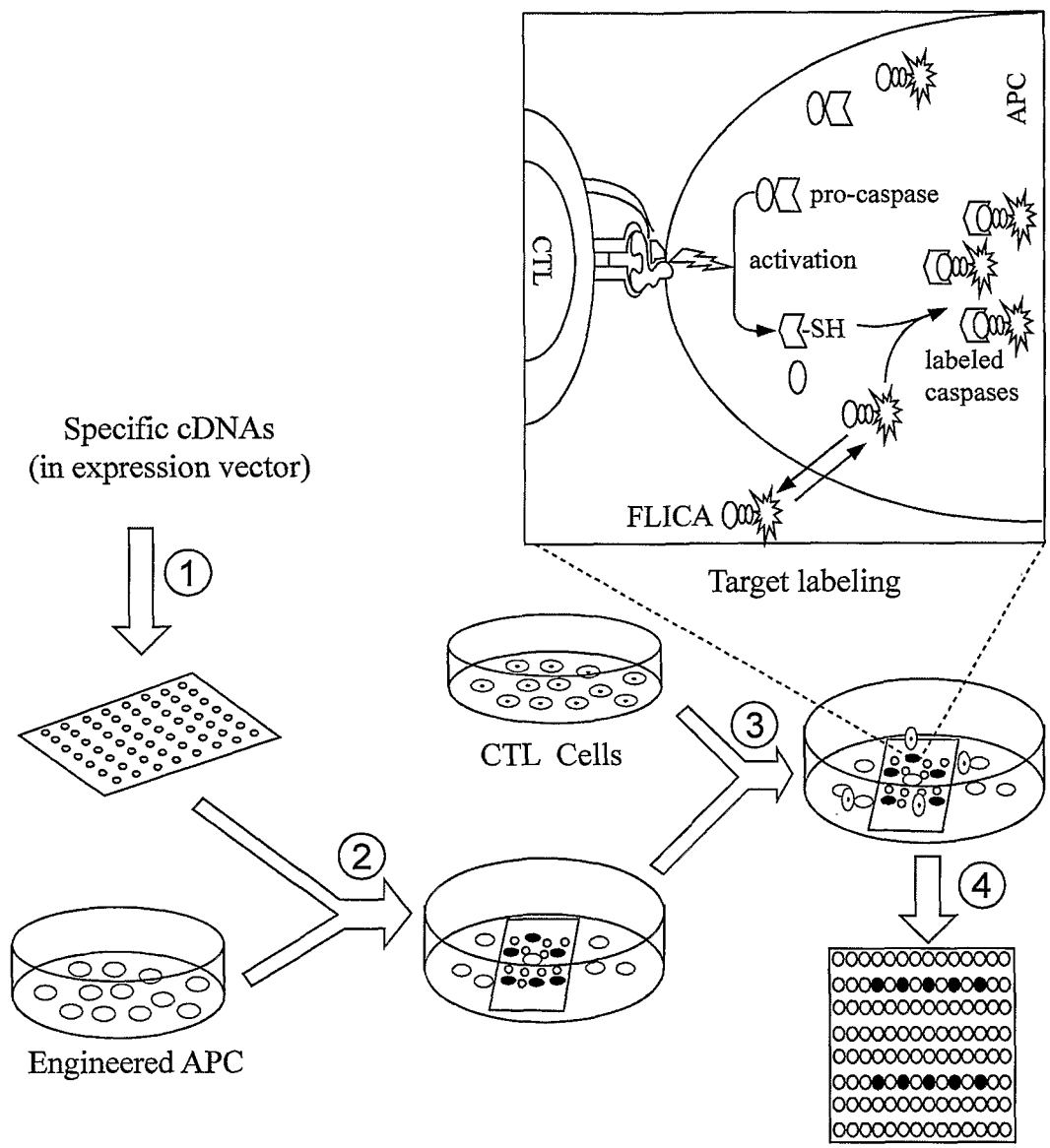
FIG. 1 is a schematic showing microarray reverse transfection and screening for CTL reactivity. (1) DNA spotting. Specific cDNAs in vectors are spotted in complex with Effectene transfection reagent in gelatin on microarray slides in a specific pattern. (2) Reverse transfection. Engineered $D^{b+}B7.1^+293T$ cells seeded on DNA microarray, express specific antigens at defined locations on the array. (3) Antigen-specific CTL killing. CTL specifically induce apoptosis in antigen-expressing targets on microarray. (4) Image-based fluorometric detection. CTL induced apoptosis is detected through affinity labeling of active caspases in apoptotic cells by cell permeable FLICA, and expanded image.

"Antigen presenting cell" or "APC" as used herein refers to a eukaryotic cell that is capable of, or can be modified to be capable of, expression a target polynucleotide encoding a polypeptide of interest, and processing the polypeptide for presentation of antigen to a cytolytic T lymphocyte (CTL), on class I MHC.

The terms "cytolytic T lymphocyte", "cytotoxic T lymphocyte", "cytolytic T cell", "cytotoxic T cell", and "CTL" are used interchangeably herein to refer to an immune cell that, through antigen-specific interaction with a peptide antigen presented in MHC Class I on the surface of an APC, induces antigen-specific killing of the APC.

The term "binds specifically" or "specific interaction" or "antigen-specific interaction" or "specifically recognize" are used substantially interchangeably in the context of an antigen-specific CTLs (CD8$^+$ T lymphocytes) to refer to the phenomenon of binding, including transient binding, of a CTL to a particular peptide presented in a class I MHC molecule on a target cell, but not substantially to a different peptide presented in a class I MHC molecule on a target cell. In this context, "antigen-specific CTL-APC interactions" are those capable of initiating apoptosis in the target APC in an antigen-specific manner (through specific binding interactions between the CTL and the APC).

"Antigen-specific CTL-APC interactions" detectable using the methods of the invention are those capable of initiating apoptosis in the target APC, which initiation of apoptosis is detected by activation of an APC caspase to cleave or otherwise modify a fluorogenic caspase substrate. In some contexts, the specification refers to "antigen-specific killing", which is meant to refer to not only to actual death of APCs as a result of antigen-specific CTL-APC interactions, but also to the initiation of apoptosis as detected by caspase activation.

As used herein, the terms "antigen-specific killing", "specific lysis", or "antigen-specific lysis" refer to initiation "specific lysis" refers to the phenomenon that results from initiation of apoptosis in a target cell (target APC) based on the presentation on its cell surface of a peptide antigen to an antigen-specific CTL that recognizes such peptide/MHC complex, which peptide antigen can be derived from a particular protein, peptide, glycoprotein, glycolipid, or lipoprotein and the like. Specific CTL-APC interactions can be readily distinguished from non-specific CTL-ACP interactions through the use of appropriate controls, e.g., a control cell (e.g., a cell of the same cell type or a cell of same cell line, which cell may optionally contain a control vector used to facilitate transfer and expression of target polynucleotides, but lacks a target polynucleotide coding sequence). As will be readily apparent to the ordinarily skilled artisan from context of use, "antigen-specific killing", "specific lysis", or "antigen-specific lysis" are used interchangeably herein in reference to a CTL-APC interaction is a shorthand, convenient reference which encompasses initiation of killing as well as actual cell death, although the latter is not required for detection of antigen-specific CTL-APC interactions using the inventive methods.

As used herein, the term "nucleic acid" and "polynucleotides" are used interchangeable herein to refer to deoxyribonucleic acid (DNA), and, where appropriate, ribonucleic acid (RNA), and usually refers to nucleic acid capable of being expressed in a host cell, more particularly an antigen presenting cell following array-based transfection. "Complementary DNA" (or "cDNA") as used herein includes recombinant nucleic acid which is suitable for expression without the need for splicing to remove any intronic sequence that may have been present in the nucleic acid from which the cDNA may have been derived.

It should be noted that where abbreviations are used to refer to nucleotides (also referred to as bases), including abbreviations that refer to multiple nucleotides. As used herein, G=guanine, A=adenine, T=thymine, C=cytosine, and U=uracil. In addition, R=a purine nucleotide (A or G); Y=a pyrimidine nucleotide (A or T (U)); S=C or G; W=A or T (U); M=A or C; K=G or T (U); V=A, C or G; and N=any nucleotide (A, T (U), C, or G). Nucleotides can be referred to throughout using lower or upper case letters. It is also understood that nucleotides sequences provided for DNA in the specification also represent nucleotide sequences for RNA, where T is substituted by U.

The terms "deoxyribonucleic acid" and "DNA" as used herein mean a polymer composed of deoxyribonucleotides.

The terms "ribonucleic acid" and "RNA" as used herein refer to a polymer composed of ribonucleotides. Where sequences of a nucleic acid are provided using nucleotides of a DNA sequence, it is understood that such sequences encompass complementary DNA sequences and further also encompass RNA sequences based on the given DNA sequence or its complement, where uracil (U) replaces thymine (T) in the DNA sequence or its complement.

As used herein, the terms "heterologous nucleic acid" and "foreign nucleic acid" refer to a nucleic acid, e.g., DNA or RNA, that does not occur naturally as part of the genome of a host cell in which it is present as a genomic or episomal element, or which is found in a location or locations in the genome that differs from that in which it occurs in nature. Heterologous DNA is usually not endogenous to the cell into which it is introduced, but has been obtained from another cell. Examples of heterologous nucleic acid of particular interest include test polypeptides, which polypeptides are of interest for generating test CTL antigens for presentation on a recombinant APC.

As used herein, the terms "target nucleic acid", "target polynucleotide" and "target sequence" are used interchangeably herein to refer to a nucleic acid encoding a polypeptide of interest (often referred to herein as a "target polypeptide" or "target antigen"), where the target polynucleotide is capable of being expressed in a recombinant host cell produced by array-based transfection, and the expressed polypeptide processed for antigen presentation the resulting recombinant APC.

"Disease antigen" as used herein refers to an antigen derived from a polypeptide, which antigen is indicative of the presence of, or prior exposure of, a subject to a disease or condition.

The terms "polypeptide" and "protein", used interchangeably herein, refer to a polymeric form of amino acids of any length, and as used herein generally refers to amino acids that are genetically encodable. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified. The term "isolated" encompasses instances in which the recited material is unaccompanied by at least some of the material with which it is normally associated in its natural state, preferably constituting at least about 0.5%, more preferably at least about 5% by weight of the total material in a given sample (e.g., total protein weight or total nucleic acid weight). For example, the term "isolated" with respect to a polynucleotide generally refers to a nucleic acid molecule devoid, in whole or part, of sequences normally associated with it in nature; or a sequence, as it exists in nature, but having heterologous sequences in association therewith; or a molecule disassociated from the chromosome.

"Purified" as used herein means that the recited material comprises at least about 75% by weight of the total material present in a composition (e.g., of total nucleic acid or of total protein), with at least about 80% being preferred, and at least about 90% being particularly preferred. As used herein, the term "substantially pure" refers to a compound that is removed from its natural environment and is at least 60% free, preferably 75% free, and most preferably 90% free from other components with which it is naturally associated.

A polynucleotide "derived from" or "specific for" a designated sequence, such as a target sequence of a target polynucleotide, refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding to, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived or specific for. Polynucleotides that are derived from" or "specific for" a designated sequence include polynucleotides that are in a sense or an antisense orientations relative to the original polynucleotide.

By "transfection" is meant introduction of nucleic acid into a host cell, which nucleic acid may be present in the host cell as an episomal element or may be integrated into the recipient host cell chromosome. The host cells generated using the reverse transfection methods in connection with the present invention can be transiently or stably transfected, and usually preferably are at least stably transfected.

"Recombinant" as used herein to describe a nucleic acid molecule refers to a polynucleotide of genomic, cDNA, mammalian, bacterial, viral, semisynthetic, synthetic or other origin which, by virtue of its origin, manipulation, or both is not associated with all or a portion of the polynucleotide with which it is associated in nature. The term "recombinant" as used with respect to a protein or polypeptide means a polypeptide produced by expression of a recombinant polynucleotide.

A "control element" refers to a polynucleotide sequence which aids in the transcription and/or translation of a nucleotide sequence to which it is linked. The term includes promoters, transcription termination sequences, upstream regulatory domains, polyadenylation signals, untranslated regions, including 5'-UTRs and 3'-UTRs and when appropriate, leader sequences and enhancers, which collectively provide for or facilitate the transcription and translation of a coding sequence in a host cell.

A "fluorescent indicator" refers to an indicator that is fluorescent, and a "fluorogenic indicator" refers to an indicator that that when modified (e.g. by interaction with its target molecule) alters (e.g. increases or decreases) its fluorescence. A "fluorogenic indicator" or "fluorogenic composition" is an indicator (indicator composition) of this invention that produces a fluorescent signal.

The term "fluorescence" is well known in the art. In the context of a fluorescent dye, the term refers to a dye that can be excited at one wavelength of light following which it will emit light at another wavelength. Excitation generally occurs at a wavelength in the range of from about 250 to 750-nm. Emitted wavelengths are generally in the range of from about 200 nm to about 300 nm, from about 300 nm to about 400 nm, from about 380 nm to about 400 nm, from about 400 nm to about 430 nm, from about 430 nm to about 500 nm, from about 500 nm to about 560 nm, from about 560 nm to about 620 nm, from about 620 nm to about 700 nm, from about 700 nm to about 1.5 µm, from about 1.5 µm to about 20 µm, or from about 20 µm to about 1000 µm.

A fluorophore (fluorescent dye) that is "distinguishable" from another fluorophore using standard detection methods and devices (e.g., fluorescence microscopy), refers to the fact that the spectral properties of the two fluorophores being compared are detectably different from one another, e.g., the emission of a given fluorophore differs from the emission of a second fluorophore by at least about 10 nm to about 15 nm, from about 15 nm to about 20 nm, from about 20 nm to about 25 nm, from about 25 nm to about 30 nm, from about 30 nm to about 35 nm, from about 35 nm to about 40 nm, from about 40 nm to about 45 nm, from about 45 nm to about 50 nm, from about 50 nm to about 55 nm, from about 55 nm to about 60 nm, from about 60 nm to about 65 nm, from about 65 nm to about 70 nm, from about 70 nm to about 75 nm, from about 75 nm to about 80 nm, from about 80 nm to about 85 nm, from about 85 nm to about 90 nm, from about 90 nm to about 95 nm, from about 95 nm to about 100 nm, from about 100 nm to about 120 nm, from about 120 nm to about 140 nm, from about 140 nm to about 160 nm, from about 160 nm to about 180 nm, or from about 180 nm to about 200 nm, or more. In the context of the present invention, such distinguishable fluorophores may be used to distinguish a fluorophore that provides a detectable signal upon induction of caspase activity (e.g., as in a fluorogenic caspase substrate) from a fluorophore used as a control to verify expression of a target polynucleotide (e.g., as in a reporter protein, such as GFP).

As used herein, a "biological sample" refers to a sample of tissue or fluid isolated from a subject. Where the biological sample is to be contacted with a recombinant APC array according to the invention, "biological sample" generally refers to samples suspected of containing an antigen-specific cytolytic T cell (CTL), which samples, after optional processing, can be analyzed in an in vitro assay. Typical samples of interest include any source in which CTLs may be found, including but not necessarily limited to, blood, plasma, serum, fecal matter, urine, saliva, milk, organs (e.g., thymus, lymph node, spleen), biopsies (e.g., thymus, lymph node, and spleen), and secretions of the intestinal and respiratory tracts. In general, biological samples can also include samples comprising in vitro cell culture constituents including but not limited to conditioned media resulting from the growth of cells and tissues in culture medium, e.g., recombinant cells, and cell components. Biological samples also encompass primary cells, or cells derived therefrom and the progeny thereof. The definition also includes samples that have been manipulated in any way after their procurement, such as by treatment with reagents; washed; or enrichment for certain cell population, such as lymphocytes, particularly CTLs, and the like. The term "biological sample" encompasses a clinical sample, and also includes cells in culture (primary cells or clones of such cells), tissue samples, organs, bone marrow, and the like.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

"Analytical specificity" as used herein refers to the ability of a detection system to specifically detect a CTL-APC cytotoxic interaction (e.g., a CTL-APC interaction that results in induction of apoptosis in the APC) and not provide for a significant detectable signal that may be associated with cells that are not undergoing such a CTL-APC cytotoxic interaction.

"Analytical sensitivity" in the context of the methods refers to the number of CTL-APC cytotoxic events that are measurable using the methods of the invention, e.g., detection of a positive result can be indicated with only a few (e.g., as few as 1, 2, 3, 4, 5, 6, 7, 8, 9, 10, 20, 25, 30, 35, etc.) reactive CTLs present in a sample. For example, the methods of the invention are of such as sensitivity that a CTL-APC cytotoxic event can be detected at the single cell level.

The terms "individual," "host," "subject," and "patient," used interchangeably herein, refer to a mammal, including, but not limited to, murines, simians, humans, mammalian farm animals, mammalian sport animals, and mammalian pets.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to a "CTL" includes a plurality of such CTLs and reference to "APC" includes reference to one or more APCs and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The practice of the present invention will employ, unless otherwise indicated, conventional methods of chemistry, biochemistry, recombinant DNA techniques and immunology, within the skill of the art. Such techniques are explained fully in the literature. See, e.g., Fundamental Virology, 2nd Edition, vol. I & II (B. N. Fields and D. M. Knipe, eds.); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Oligonucleotide Synthesis (N. Gait, ed., 1984); A Practical Guide to Molecular Cloning (1984).

The invention will now be described in more detail.

DETAILED DESCRIPTION OF THE INVENTION

The invention is based on the discovery of methods for the rapid and sensitive detection of antigens recognized by antigen-specific cytolytic T lymphocytes (CTLs), which methods are amenable to high-throughput.

In general, the invention relates to methods for identifying T cell antigens specifically recognized by a CTL by contacting antigen-specific CTLs with an array having on a surface a plurality of recombinant target APCs located at a plurality of locations on the array surface, where the target APCs express different recombinant antigens, which antigens are processed for presentation to the CTL (on Class I MHC). Usually, the plurality of recombinant target APCs on the array express a plurality of different recombinant antigens, with the recombinant target APCs being provided on the array as distinct features at defined locations (addressable locations), thus allowing for correlation with antigen-specific CTL reactivity with a target APC of a feature at a defined location with the target polynucleotide present on the array and expressed in the target APC at that location.

Antigen-specific CTL-APC-mediated killing is detected by induction of activity of caspase upon a fluorogenic caspase substrate, such that an increase in a fluorescent signal which serves as a marker of induction of apoptosis of the target APC and thus identity of a CTL antigen encoded by the target polynucleotide expressed in the target APC.

FIG. 1 provides an exemplary schematic of a method of the invention. In this example, a target DNA encoding a polypeptide of interest (e.g., cDNAs in expression vectors) is spotted along with a transfection agent (or "carrier") on the microarray slides in a specific pattern (FIG. 1, (1)). For example, the DNA can be provided as a complex with Effectene™ transfection reagent in gelatin. The DNAs are spotted on the array in a specific pattern so as to provide distinct features having specific locations or "addresses". Each feature thus has a known target DNA and can be identified by virtue of its "address" on the array.

FIG. 1, reference (2) denotes the reverse transfection step, in which host cells which can serve as APCs are seeded on the DNA microarray under conditions suitable to provide for introduction of the DNA into the host cell, thus providing a recombinant target APC. In a specific example, the host cell is a mammalian cell (e.g., 293T cells) engineered to express a MHC complex (e.g., $D^{b+}B7.1^+$). The resulting array contains target APCs (recombinant host cells) that express specific antigens at defined locations on the array. Stated differently, the array produced has a plurality of features, which features include target APCs express and present an antigen of interest in a MHC complex, where the plurality of features have different antigen-expressing target APCs.

The target APCs are loaded with a cell permeable, fluorogenic caspase substrate, such as fluorochrome-labeled inhibitors of caspases (FLICA). Exemplary FLICAs include derivatives of valyalanylaspartic acid fluoromethyl ketone (z-VAD-FMK), which detects drug-induced apoptosis through affinity labeling of active caspases.

The array is contacted with CTLs under conditions suitable for antigen-specific CTL-APC interaction. CTLs that specifically recognize an antigen presented on an APC induce apoptosis in the APC, which in turn results in induction of caspase activity, which in turn results in modification of the fluorogenic caspase substrate, such as a fluorochrome-labeled inhibitors of capases (FLICA), so as to provide a detectable signal in target APCs that are the target of CTL reactivity (illustrated in FIG. 1, (3), and inset). As illustrated in FIG. 1, (4), image-based fluorometric detection is used to identify features on the array that are associated with the detectable fluorescent signal generated by the induction of apoptosis in one or more target APCs in that feature. Such features are thus "positive" for CTL-mediated killing, and thus contain target DNA encoding a CTL antigen.

Surprisingly, the methods of the invention provide sensitive and rapid assays that provide for direct screening of T cells for reactivity to a target APC at the for identifying antigen-specific CTL-APC interactions at individual microarray spots at the single cell-to-cell interaction level. The assays of the invention can be used in a variety of applications, such as identification of antigens recognized by a CTL and, in other embodiments, detection CTLs having a known antigen specificity in a biological sample.

The ability to express large numbers of cDNAs simultaneously at discreet addresses on microarrays, combined with detection of CTL-induced apoptosis of APCs measured by FLICA retention on those arrays, offers an advanced strategy for high throughput identification of cDNAs encoding MHC class I-restricted antigens recognized by CTLs. Since the CTL microarray assay involves detection of active forms of highly conserved caspase enzymes, the methods of the invention are feasible for several mammalian species, including humans (where the MHC-expressing APC is a relevant HLA-expressing APC). The methods of the invention, to which the inventors refer to as "CTL Array" technology, will significantly accelerate the screening process for identifying tumor or virus specific antigens on a genome-wide scale, thereby expanding the repertoire of candidate antigens for clinical vaccine development and immunotherapies. The CTL Array technology of the invention can also be used in diagnostic settings to facilitate detection of CTLs reactive with, for example, a T cell antigen of a pathogen (e.g., virus or other intracellular pathogen), an autoimmune disorder, and the like.

The compositions and methods of the invention will now be described in more detail.

Cell-Based Arrays

The cell-based arrays for use in the invention are generally composed of an array having adherent target APCs (recombinant host cells) at defined locations on the array, which target APCs are recombinant cells produced by transfection with target polynucleotide spotted at the defined locations. The target APCs thus express a recombinant antigen of interest encoded by the target polynucleotide. Exemplary materials for the various components of the array, as well as exemplary methods of making such arrays, are described below in more detail.

Host Cells for Use as Recombinant Target Antigen Presenting Cells (APCs) on Arrays Any suitable host cell capable of adhering to a defined location on an array surface, capable of expressing a target polynucleotide encoding a polypeptide, capable of antigen processing, and is capable of, or can be modified to be capable of, providing for presentation of the processed polypeptide for presentation of antigen to a cytolytic T lymphocyte (CTL) (on class I MHC) is a suitable host cell for use in the invention. In general, such a suitable host cell is referred to herein as "antigen presenting cell" or "APC", which, as noted above, refers to a eukaryotic cell that is capable of, or can be modified to be capable of, expression a target polynucleotide encoding a polypeptide of interest, and processing the polypeptide for presentation of antigen to a cytolytic T lymphocyte (CTL), on class I MHC.

In one embodiment, the host cells as "professional APCs", which cells include macrophages and dendritic cells. Methods for isolating such cells for use as host cells in the methods of the invention are well known in the art. For example, antibodies specific for a cell surface marker indicative of an APC of interest can be used to facilitate isolation of a specific population of APCs. For example anti-CD11b/c and/or anti-CD34 antibodies can be attached to the surface of a bead (e.g., magnetic bead) to provide for isolation of dendritic cells.

In another embodiment, the host cell is an engineered APC. For example, a eukaryotic cell, usually a mammalian cell (usually of the same species as the CTL source, e.g., a human cell where the CTLs are from human) can be modified to express a desired MHC Class I molecule, as well as any necessary co-stimulatory molecules, such as B7-1 and B7-2 molecules, which co-stimulatory molecules are recognized by receptors on the surface of the CTL (e.g., CD28 or CTLA-4, the receptors for B7 on the T cell surface). Nucleic acids encoding a number of different MHC Class I molecules, as well as nucleic acids encoding such co-stimulatory molecules, are well known in the art.

In one embodiment, the host cell used to generate a target APC is a "null" cell that is deficient or lacks detectable alloreactive MHC molecules on the cell surface (so as to avoid alloreactivity with effector CTLs) and expresses or is modified to express a desired Class I MHC complex to provide for antigen presentation to the effector CTLs of interest. Exemplary null cells useful in the methods of the invention are known in the art, as at methods and compositions to provide for production of recombinant null cells that can serve as APCs useful in the present invention.

In general, to avoid high background levels of caspase activity induction and reduce the incidence of false positive results, host cells for transfection on the arrays should be selected so as to avoid alloreactivity with the CTLs to be screened. Thus, the host cells to be used as target APCs should generally be selected so as to be MHC-matched with the subject from whom the CTLs to be screened are obtained. Methods for MHC typing, and methods of selecting or modifying a host cell for use as an MHC-matched APC are known in the art.

Arrays Having Bound Target Polynucleotide Encoding Antigens of Interest for Expression in Host Cells on Array Any suitable method of making arrays having a DNA of interest for use in transfecting cells, and any suitable method of transfecting cells using such arrays can be applied in the practice of the present invention. For example, US 2002/0006664; US 2003/0228694; US 2003/0228601; US 2003/0203486; and U.S. Pat. No. 6,544,790, which published applications and patents are specifically incorporated by reference herein in their entireties. Exemplary arrays as may be suitable for use in the present invention are discussed in more detail below.

Target Polynucleotides Encoding Polypeptides of Interest for Antigen Presentation Target polynucleotides include any polypeptide-encoding nucleic acid which is adapted for expression in a host cell to provide a recombinant APC for use on the arrays useful in the methods of the invention. In general, a target polynucleotide can be any nucleic acid encoding a polypeptide of interest, where the target polynucleotide is capable of being expressed in a recombinant host cell produced by array-based transfection, and the expressed polypeptide processed for antigen presentation the resulting recombinant APC.

The target polynucleotide can be, for example, DNA, RNA or modified or hybrid forms thereof, with the proviso such are capable of being expressed in a recombinant APC. The target polynucleotide may be from any of a variety of sources, such as nucleic acid isolated from cells, or that which is recombinantly produced or chemically synthesized.

The target polynucleotide can encode a polypeptide of any length, including a full-length polypeptide, or polypeptide fragment, particularly a fragment that provides a T cell antigen that is presented in Class I MHC for recognition by a CTL specific for that antigen.

The target polynucleotide can be from any suitable source. For example, the transfection array can include coding sequence from cDNAs or genomic DNA. Where the target polynucleotide is naturally occurring, those sequences can be isolated from any organism or collections of organisms. In addition to native sequences, the coding sequences can include those which have been mutated relative to the native sequence, e.g., a coding sequence that differs from a naturally occurring sequence by deletion, substitution or addition of one or more residues Target polynucleotide can also be generally by recombinant or synthetic techniques, the latter being most applicable to relatively short nucleic acids. Target polynucleotides can be generated to have randomized sequences, with the proviso that at least one open reading frame for expression of a polypeptide is provided.

The target polynucleotide sequences can be present as part of a larger vector, such as an expression vector (e.g., a plasmid or viral-based vector), although such may not be necessary for introduction and expression of a target polynucleotide. The target polynucleotide can be introduced into cells in such a manner that at least a sequence defining a coding sequence is integrated into the genomic DNA and is expressed. Alternatively, the target polynucleotide can remain as an extrachromosomal element (e.g., is maintained episomally).

The target polynucleotide as provided on the array for transfection can be linear or circular, double stranded or single stranded, and can be of any size suitable for uptake by the host cell. In certain embodiments, especially where traditional expression vectors are used, the target polynucleotide is from about 200 nt to about 10 kb in size, usually from about 200 nt to about 5 kb, and more usually from about 200 nt to 2 kb. Target polynucleotide can be provided as part of a larger polynucleotide (e.g., as when provided in an expression vector), and in such embodiments can be from about 1 kb to about 15 kb, usually from about 5 kb to about 8 kb.

It is generally desirable that a recombinant target APC produced using the reverse transfection technique described herein will be maintained in the cells and its progeny, i.e., will be capable of replication with and/or in the host cell. It may be a DNA which is integrated into the host genome, and thereafter is replicated as a part of the chromosomal DNA, or it may be DNA which replicates autonomously, as in the case of a episomal element. In the latter case, the vector will generally include an origin of replication which is functional in the host. In the case of an integrating vector, the vector may include sequences which facilitate integration, e.g., sequences homologous to host sequences, or encoding integrases. The use of retroviral long terminal repeats (LTR) or adenoviral inverted terminal repeats (ITR) in the construct of the transfection array can, for example, facilitate the chromosomal integration of the construct.

The expression vectors may comprise regulatory elements such as an operably linked promoter, enhancer(s), and/or other 5' and/or 3' flanking nontranscribed sequences. The expression vectors can further comprise 5' and/or 3' untranslated sequences, such as ribosome binding sites, a polyadenylation site, splice and transcriptional termination sequences. Exemplary vectors include, but are not limited to, cytomegalovirus (CMV) promoter-based vectors, MMTV promoter-based vectors, and SV40 promoter-based vectors.

Certain eukaryotic (including mammalian) expression vectors provide for propagation of the vector in bacteria (such as in an amplification step after recovery from the array). Some of these vectors are modified with sequences from bacterial plasmids, such as pBR322, to facilitate replication and drug resistance selection in both prokaryotic and eukaryotic cells. The various methods employed in the preparation of the plasmids are well known in the art.

Polypeptides Encoded by Target Polynucleotides

The polypeptides encoded by the target polynucleotides can be any polypeptide of interest, including polypeptides for which identification of a CTL epitope (if present) is desired, and polypeptides having a known CTL epitope. The polypeptides can be derived from a naturally-occurring polypeptide, or can be wholly recombinant or synthetic, as in randomized polypeptides.

In one embodiment the target polynucleotide encodes a polypeptide of a cancerous (neoplastic) cell. Such cancers may be associated with solid or semisolid tumors. Exemplary cancers for which identification of CTL antigen is of interest include, but are not limited to lymphomas (e.g., Hodgkin's, non-Hodgkin's), leukemia, carcinoma, lymphoma, astrocytoma, sarcoma, glioma, retinoblastoma, melanoma, Wilm's tumor, bladder cancer, breast cancer, colon cancer, hepatocellular cancer, pancreatic cancer, prostate cancer, Lung cancer, liver cancer, stomach cancer, cervical cancer, testicular cancer, renal cell cancer, brain cancer, and the like.

In one embodiment, the target polynucleotide encodes a polypeptide of an intracellular pathogen (e.g., virus, bacterium, fungi, parasites, and the like). "intracellular pathogen" refers to any organism that exists within a host cell, either in the cytoplasm or within a vacuole, for at least part of its reproductive or life cycle.

Exemplary viral intracellular pathogens from which target polynucleotides encoding a polypeptide of interest may be derived include hepatitis (e.g., HBV, HCV, HDV, hepatitis A), retroviruses (e.g., HIV, HTLV-1, HTLV-II), influenza, smallpox, adenovirus, cytomegalovirus, Epstein-Barr virus, HSV (e.g., HSV1, HSV2, HSV6), varicella-zoster virus, papilloma virus, erythrovirus, polyomaviruses (e.g., BK, JC) measles virus, and rubella virus.

Exemplary bacterial intracellular pathogens from which target polynucleotides encoding a polypeptide of interest may be derived include *Mycobacteria* (e.g., *M. tuberculosis, M. leprae*), *Chlamydia, Salmonella* (e.g., *S. typhi*), *Legionella, Brucella, Shigella, Neisseria, Staphylococcus, Listeria*, enteropathogenic *Escherichia coli* (EPEC), enterohaemorrhagic *Escherichia coli* (EHEC), *Yersinia, Brucella, Coxiella, Rickettsia*, and the like).

Other exemplary intracellular pathogens include protozoa (e.g., Taxoplasma), fungi, intracellular parasites (e.g., *Plasmodium* (e.g., *P. vivax, P. falciparum, P. ovale*, and *P. malariae*), *Leishmania, Trypanasoma, Toxoplasma*), and prions.

Other target polynucleotides of interest are those encoding a polypeptide that is derived from an autoimmune antigen or putative autoimmune antigen.

In other embodiments, the target polynucleotides encode a library of polypeptides, which polypeptides can have randomized sequences. In other embodiments, the subject array can be made of a library of related sequences modified relative to one another to provide for a library of encoded polypeptides, which polypeptides in turn may be processed to provide for different Class I antigens. Methods for generating one or more mutants given a desired cDNA are known in the art.

In general, antigenic peptides produced by antigen processing of recombinant polypeptide encoded by the target polynucleotide is of a length compatible with presentation with a Class I MHC complex. Such antigenic peptides are usually from about 6 to 12 amino acids in length, usually from about 8 to 10 amino acids. In general, such antigenic peptides that render a target APC susceptible to CTL-mediated killing contain a T cell epitopes. The epitopic sequences from a number of antigens are known in the art, and may be incorporated for use in screening in the assays of the invention. Alternatively, the epitopic sequence may be empirically determined using the methods of the invention (e.g., by using deletion mutants of a selected polypeptide).

Arrays Having Target Polynucleotides

Any suitable method of making arrays having a DNA of interest for use in transfecting cells, and any suitable method of transfecting cells using such arrays can be applied in the practice of the present invention. For example, US 2002/0006664; US 2003/0228694; US 2003/0228601; US 2003/0203486; and U.S. Pat. No. 6,544,790, which published applications and patents are specifically incorporated by reference herein in their entireties.

Array Substrate

Any suitable surface which can be used to affix the nucleic acid containing mixture to its surface can be used. For example, the surface can be glass, plastics (such as polytetrafluoroethylene, polyvinylidenedifluoride, polystyrene, polycarbonate, polypropylene), silicon, metal, (such as gold), membranes (such as nitrocellulose, methylcellulose, PTFE or cellulose), paper, biomaterials (such as protein, gelatin, agar), tissues (such as skin, endothelial tissue, bone, cartilage), minerals (such as hydroxylapatite, graphite). Additional compounds may be added to the base material of the surface to provide functionality, with the proviso such do not adversely affect the detection methods as set out in the present invention.

The substrate may be a porous solid support or non-porous solid support. The surface can have concave or convex regions, patterns of hydrophobic or hydrophilic regions, diffraction gratings, channels (e.g., microfluidics channels) or the like. The surface can be planar, planar with raised or sunken elements, fibers (e.g. fiber optic bundles), tubular (both interior or exterior), a 3-dimensional network (such as interlinking rods, tubes, spheres) or other shapes. Where the transfection array is provided on the end of a fiber optic system, such as a fiber optic bundle, changes in caspase activity in the cells on the array in response to CTLs as detected by the fluorogenic caspase substrate can be detected spectrometrically by conductance or transmittance of light over the spatially defined optic bundle.

The surface can be part of an integrated system. For instance, the surface can be the bottom of a microtitre dish, a culture dish, a culture chamber. In general, the material of the substrate and geometry of the array will be selected based on criteria that it be useful for automation of array formation, maintaining the recombinant target APCs on the surface, contacting the CTLs with the target APCs, and detection of induction of apoptosis of the APCs were an antigen-specific CTL-APC interaction occurs.

Characteristics of DNA on Array

The DNA can be provided on the array in a variety of different configurations. For example, the number of different DNAs on the array can vary greatly according to the needs of the assay. For example, a single array can provide at least 10 different DNAs, usually at least 100, 500, 750, 1000, 1250, 1500, or 2000 different DNAs per square centimeter, where the different DNAs have discrete sequences. Preferably, where the array substrate is a planar surface, the target sequences are arrayed in an addressable fashion, such as rows and columns.

The DNAs are provided as discrete features on the array surface. The term "feature", as it is used in describing a transfection array, refers to an area of a substrate having a known collection of a target polynucleotide sequences encoding an antigen of interest or, where the array has been used in a cell-based transfection procedure, a collection of recombinant target APCs that are recombinant for a known collection of recombinant target sequences. One feature is different than another feature if the target sequences of the different features have different nucleotide sequences.

Usually the feature defines an area having a homogenous collection of target polynucleotide sequences, or homogenous collection of recombinant target APCs, such that, for example, the population of recombinant target APCs present at any one feature contain the same recombinant target polynucleotide sequences. Usually the arrays are designed so as to provide for production of recombinant target APCs containing a single recombinant target polynucleotide encoding an antigen of interest, which antigen may be either a known CTL antigen or a candidate CTL antigen. However, features having a population of different target polynucleotides, so as to provide for production of a feature containing a population of recombinant target APCs that contain two or more recombinant target polynucleotides encoding different antigens are also contemplated. In these embodiments, the target polynucleotide populations (and thus the recombinant target APC population) present in the feature may be homogenous or heterogenous, usually homogenous.

In some embodiments, the features on the array contain a heterogenous population of target polynucleotide sequences for production of a heterogenous population of recombinant target APCs, different target polynucleotides encoding different antigens of interest. Such features on the array can be produced by pooling different target sequences, and spotting the pooled target sequences at a defined (addressable) location. In such embodiments, where killing of a target APC is detected after contact with an antigen-specific CTL at a feature having a heterogenous target APC population, additional screening may be conducted using arrays having homogenous features representing the different pooled recombinant target APCs from the heterogenous feature to facilitate identification of the target APC(s) in the heterogenous feature that presented an antigen reactive with the CTL(s) (e.g., the pooled target sequences are split among different features on a second array, and again screened with the CTL).

If each feature size is about 100 microns on a side, each array may have about 100, 500, 750, 1000, 1250, 1500, or 2000 target sequence addresses (features) in a one square centimeter area. In certain preferred embodiments, the transfection array provides a density of at least 100, usually at least 103 different features per square centimeter (103 sequences/cm$^2$), and may have more as the limits of the assay allow (e.g., at least $10^4$ features/cm$^2$, $10^5$ features/cm$^2$, or $10^6$ features/cm$^2$).

In some embodiments it may be desirable to provide multiple different target sequences in each feature, e.g., in order to promote co-transfection of the host cells with at least two different target sequences, so as to provide for expression of the gene products encoded by each of the two different target sequences. Co-transfections can be accomplished by including the two or more target polynucleotides in the solution spotted on the array surface. Usually, the collection of different target sequences in one feature should be distinct from other features of the array, however, it may be desirable to provide for co-transfection of a control target sequence which can act as a marker for expression and/or transfection.

Production of Arrays and Transfection Of Host Cells to Produce Recombinant APC Target Cells The DNA encoding a polypeptide of interest is deposited (e.g., spotted or placed in small defined areas) onto a surface (e.g., a slide or other flat surface, such as the bottoms of wells in a multi-welled plate) in defined, discrete (distinct) locations and allowed to dry, with the result that the DNA-containing mixture is affixed to the surface in defined discrete locations. Such locations are referred to herein, for convenience, as defined locations.

The DNA can be deposited in as many discrete locations as desired, and in any pattern desired. The resulting product is a surface bearing the DNA in defined discrete locations; the identity of the DNA present in each of the discrete locations (spots) is known/defined. The size of the DNA spots and the density of the DNA spots affixed to the surface can be adjusted depending on the conditions used in the methods. For example, the DNA spots can be from about 100 µm to about 200 µm in diameter, usually about 100 µm to about 150 µm in diameter, and can be affixed from about 200 µm to about 500 µm apart on the surface. Spots of such size on an array can provide for, for example about 1500-2500 spots per standard slide array.

In general, the DNA is deposited on the array surface as a mixture with a carrier which facilitates transfection. The carrier can be any suitable material, such as gelatin, a hydrogel (e.g., polycarboxylic acid, cellulosic polymer, polyvinylpyrrolidone, maleic anhydride polymer, polyamide, polyvinyl alcohol, or polyethylene oxide), or an appropriate lipid-based transfection reagent (e.g., Effectene™). The DNA-containing mixture is spotted onto a surface, such as a slide, thus producing a surface bearing the lipid-DNA mixture in defined locations. The array is allowed to dry to affix the lipid-DNA mixture is affixed to the array surface.

After drying is complete, host cells to be reverse transfected are placed on top of the surfaces onto which the DNA-containing mixture has been affixed. Actively growing cells are generally used. The host cells (in an appropriate medium) are plated, generally at a relatively high density (such as $1\times10^5$/cm$^2$), on the array surface having the affixed DNA-containing mixture. The host cells are cultured in an appropriate medium, such as Dulbecco's Modified Eagles Medium (DMEM) containing 10% heat-inactivated fetal serum (IFS) with L-glutamine and penicillin/streptomycin (pen/strep). Other media can be used and their components can be determined based on the type of cells to be transfected.

The resulting arrays, which contain the dried DNA-containing mixture and cells into which the DNA is to be reverse transfected, are maintained under conditions appropriate for growth of the cells and entry of DNA into the cell. Usually about one to two cell cycles are sufficient for reverse transfection to occur, but will vary with the cell type and conditions used.

After sufficient time has elapsed, arrays can be assessed for transfection and/or expression of the encoded product, if desired. For example, the DNA spots can include a DNA encoding a reporter gene, which reporter gene provide a detectable signal (e.g., fluorescence, such as with GFP, YFP, and the like). The presence of fluorescence indicates that reverse transfection has occurred and the encoded protein has been expressed in the defined location(s) which show fluorescence. The presence of a signal, detected by the method used, on the slides indicates that reverse transfection of the DNA into cells and expression of the encoded product or an effect of the DNA in recipient cells has occurred in the defined location(s) at which the signal is detected. Since the identity of the DNA present at each of the defined locations is known, the identity of the expressed protein is also known.

Fluorogenic Caspase Substrates

Detection of CTL-mediated induction of apoptosis in a target cell on the array is accomplished using a cell-permeable fluorogenic caspase substrate. A "fluorogenic caspase substrate" is a peptide-based compound that, upon binding and/or cleavage by an activated caspase, provides for a detectable signal, e.g., by generating a fluorescent cleavage product that is free in the cell or by transferring a detectable label to the caspase enzyme with which it interacted. For example, SR-VAD-FMK is a sulforhodamine derivative of valylalanylaspartic acid fluoromethyl ketone (VAD-FMK) which is a potent inhibitor of caspase activity. The SR-VAD-FMK reagent enters the cell and covalently binds to an activated caspase, likely by covalently binding to the reactive cysteine (Cys 285) on the large subunit of a caspase heterodimer. The fluorescent label of SR-VAD-FMK is thought to be transferred to the active site of the activated caspase enzyme to provide for detection by fluorescence microscopy.

Exemplary fluorogenic caspase substrates are composed of two fluorophores (or a fluorophore and a quencher) covalently linked to a peptide (usually of about 18-amino-acids in length) containing a proteolytic cleavage site for a specific caspase or for multiple different caspases. In substrates that are not cleaved or bound to an activated caspase, fluorescence is quenched due to the formation of intramolecular excitonic dimers. Upon cleavage of the peptide by the specific caspase or other specific interaction with the activated caspase, the fluorophore-fluorophore interaction is abolished, leading to an increase in fluorescence that can be detected by fluorescence microscopy. Since caspase activation in target APC cells occurs shortly after the CTL-target APC interaction, detection of caspase activation within intact target APC cells provides an early and biologically relevant measurement of CTL-mediated apoptosis, and thus is indicative of an antigen-specific CTL-APC interaction.

In general, indicators of caspase activity include any chromophore or fluorophore labeled based caspase substrate including, cyclic or linear, mono, dipeptide, tripeptide and tetra peptide to 8, 12, 16, 20, 30, or 31 amino acid residue long peptide substrates having attached one or two chromophores or fluorophores or a combination of chromophores and fluorophores, such that the substrate in the uncleaved state (or when it is not bound to activated caspase) does not provide a detectable signal or provides a first detectable signal that can be readily distinguished from a second detectable signal that is generated following cleavage (or binding to activated caspase).

The caspase activity indicator can a fluorogenic caspase substrate that is cleaved by any suitable caspase, with the proviso that activity of the caspase is induced upon induction of apoptosis in a target cell following a CTL-APC antigen-specific interaction. Fluorogenic caspase substrates containing cleavage sequences for each of caspase 3/7 (DEVDase), caspase-9 (LEHDase), caspase-8 (IETDase), and caspase-6 (VEIDase) have been described (see, e.g., US 2003/0211548). Furthermore, fluorogenic caspase substrates can be selected so as to be cleaved earlier or later in the caspase activation cascade, as desired. For example, since caspase-6 is thought to act downstream of caspase-8 and -9, and in some cases caspase-3, in the caspase activation cascade, it might be expected that more caspase-positive cells may be detected and detected more quickly using substrates that are cleaved earlier in the apoptotic pathway.

In one embodiment of particular interest, a fluorogenic caspase substrate is used which is capable of detecting activation of multiple caspase enzymes in the target host cell (i.e., a "fluorogenic multi-caspase substrate"). For example, fluorogenic caspase substrates having the VAD peptide can provide for detection of activity of all of caspases 1-9.

In general, caspase activity indicators useful in the invention comprise a protease substrate having a fluorescence resonance energy transfer (FRET) system comprising two fluorophores or a chromophore and a fluorophore with the fluorescence of the latter quenched until the substrate is cleaved by a protease. Certain preferred indicators comprise a homo-double labeled substrate (e.g. a substrate attached to fluorophores of the same species) that form an H-dimer (see, e.g., U.S. Pat. Nos. 5,605,809, 5,714,342, and 6,037,137, and international applications WO9613607 WO 98/37226, and WO/01/18238 and various commercial reagents (e.g. PhiPhLlux™ from Oncoimmunin, Inc.). Also contemplated are substrates that form a J-dimer that results in a decrease in fluorescence when the substrate is cleaved.

CTLs for Screening

CTLs for use in the methods of the invention can be obtained from any suitable source. For example, the CTLs may be obtained from a subject who has, or is suspected to have, CTLs that are reactive with a target antigen of interest. Typical samples of interest from such subjects include any source in which CTLs may be found, including but not necessarily limited to, blood, plasma, serum, fecal matter, urine, saliva, milk, organs (e.g., thymus, lymph node, spleen), biopsies (e.g, thymus, lymph node, and spleen), and secretions of the intestinal and respiratory tracts.

For example, CTLs are obtained from a subject who has been exposed to, or is suspected to have been exposed to, an intracellular pathogen, such that the sample obtained from the subject contains or is suspected to contain CTLs reactive with an antigen of an intracellular pathogen (e.g., virus, intracellular bacteria, intracellular parasite, and the like as discussed above).

In another example, CTLs are obtained from a subject who has, or is suspected to have, cancer. Thus, samples obtained from such subjects contain or are suspected to contain CTLs reactive with tumor antigens.

In another example, CTLs are obtained from a subject who has, or is suspected to have, an autoimmune disorder which is cell-mediated. Thus, samples obtained from such subjects contain or are suspected to contain CTLs reactive with self-antigens.

CTLs can be primary cells or can be clones. In general, the number of CTLs used in the screening methods of the invention is relatively low, with usually about $1\times10^6$ cells, about $1.5\times10^6$ cells, about $2\times10^6$ cells, about $3\times10^6$ cells, or about $5\times10^6$ cells being sufficient for screening of a typical array as described in the Examples below.

Methods for isolating CTLS are well known in the art. For example, CTLs can be isolated using anti-CD8 antibodies, which may be bound to a substrate, such as a magnetic bead.

Screening Method

The methods of the invention typically involve contacting target APCs on the array with a CTL, and detecting the presence or absence of antigen-specific CTL-APC interactions by detecting the presence or absence of an activated caspase in the target APC as indicated by a detectable signal from a fluorogenic caspase substrate. Detection can involve detecting CTL-APC interactions at the single cell level (e.g., utilizing a single cell image based instrument).

In general, the methods of the invention can involve detecting the presence or absence of antigen-specific CTL-APC interactions using a plurality of target APCs contacted with a sample containing CTLs, which CTLs may share the same antigen specificity or may have different antigen specificities. In some embodiments it may be desirable to provide positive or negative control target cells (e.g., provided at one or more distinct features of the array) that have a label distinguishable from the test target APCs on the array. For example, positive control APCs can be provided that present an antigen that is known to be recognized by a positive control CTL which is included in the sample. Similarly negative control APCs can be provided that do not present an antigen for CTl recognition.

In a preferred embodiment, target APCs are "loaded" with a fluorogenic caspase substrate prior to or during incubation with the CTLs. The target cells and CTLs (effector cells) are coincubated for a time sufficient for specific interaction between target cells and CTLs, usually about 1-4 hours, although the exact time may vary (e.g., according to the host cell used as the target cell, the number of CTLs being assayed, and the like) and can be readily determined by routine methods. After a time sufficient for antigen-specific CTL interactions to occur, the array is washed, and the presence of absence of a fluorescence signal is assessed for each feature on the array (e.g., by fluorescence microscopy).

Detection

Arrays can be scanned to detect antigen-specific CTL-APC interactions by a variety of methods, e.g., simple fluorescence microscopy, scanning laser microscope, by fluorimetry, a modified ELISA plate reader, etc. For example, a scanning laser microscope may perform a separate scan, using the appropriate excitation line. The digital images generated from the scan are then combined for subsequent analysis. For any particular array feature, the ratio of the fluorescent signal prior to contacting with CTLS and after incubation with CTLs can be determined.

High-Throughput and Automated of Screening

The methods of the invention can be readily adapted for high-throughput assays, which can involve providing for automated screening to detect antigen-specific CTL-APC-mediated killing, as detected by caspase activity, which serves as a marker of induction of apoptosis of the target APC. Any or all or nearly all steps of the methods of the invention can be automated, including production of arrays for use in transfection of cells, contacting CTLs with the APC array, and detection and analysis of antigen-specific CTL interactions.

For example, methods and devices relating to systems for cell-based screening see, e.g., US 2001/0041347; US 2003/0096322; US 2004/0101912; US 2004/0063162; US 2004/0009539; US 2003/0204316; and US 2003/0096322, which describe automated systems for analysis of cells containing fluorescent reporter molecules where the cells are provided in an array of locations, where, after contacting the cells with a stimulus, images are acquired from the cells, and the acquired images analyzed to provide information about the effect of the stimulus upon the cell. In the present invention, the image acquired would indicate whether an antigen-specific CTL-APC interaction occurred (e.g., at the single cell level) within the features at one or more addressable locations on the array, where an increase in detectable signal associated with caspase activity induction indicates an antigen-specific CTL-APC interaction occurred at that feature, and further indicates the target APC contains a target polynucleotide encoding an antigen recognized by a CTL with which the array was contacted.

In general, microarray fluorescence readers, such as those typically used for expression microarray analysis, can be used to obtain data from the "CTL Arrays" described herein. The software typically associated with such microarray fluorescence readers can be applied to acquisition and analysis of data for threshold establishment (i.e., determination of a background level of fluorescence), standardization and export to other applications as desired for further analysis. Optical scanning using an automated microscope and a motorized stage can be particularly useful in high-throughput applications. Robotic loading of slides onto the microscopy platform allows a further increase in throughput. APC arrays can be marked with predetermined geographic locations that allows identification of array start and stop points. Automated data acquisition in all involved channels may be performed (for example, but not limited to brightfield/phase contrast/DIC/Color, FITC, CY5, CY3, DAPI, PI, UV, etc.). Automated analysis is also of interest, allowing automated counting of antigen-specific CTL-APC interactions (e.g., per feature), fluorescence intensity, and the like.

Applications of the Methods of the Invention

As will be readily apparent to the ordinarily skilled artisan upon reading the present disclosure, the methods of the invention find a variety of applications in a variety of settings. Exemplary applications include, but are not limited to, discovery of CTL antigens, detection of reactive CTLs in a sample (e.g., in the context of diagnosis), and other uses. Exemplary applications are described below.

Identification of Antigens Recognized by Antigen-Specific CTLs

In one embodiment, the assays of the invention are used to identify an antigen to which CTLs responded in vivo, where the antigen is derived from, for example, a cancerous cell (e.g., a malignant tumor cell, including a metastasis of a primary tumor), an intracellular pathogen, or an autoantigen. CTLs used in this screen are obtained from a subject having a disease or condition in which production of antigen-specific CTLs is suspected, and for which identification of the corresponding CTL antigen(s) is desired.

This embodiment of the invention can be used to facilitate development of vaccines, which can be based upon a single CTL antigen or a cocktail of CTL antigens. This embodiment of the invention can also be used to tailor vaccines for a given individual or population of individuals, particularly where the individual or population of individuals may have characteristics that might affect an immune response in the individual or population. Populations of individuals can be based upon a variety of different factors, such as one or more of age (e.g., children, young adults, adults), race or ethnicity (e.g., Caucasian, Afro-American, Hispanic, European (e.g., western or eastern), Asian, Middle Eastern, African, and the like), and immune status (e.g., immunocompromised, having an autoimmune condition, and the like).

Detection of Antigen-Specific CTLs Using Known T Cell Antigens

In another exemplary embodiment, the methods of the invention are used in diagnostic assay to detect an antigen-specific CTL in a sample obtained from a subject suspected of having a disease or condition. In such assays, detection of an antigen-specific CTL-APC interaction indicates the subject has elicited a CTL response to an antigen associated with a particular disease or condition (e.g., cancer, infection by an intracellular pathogen, self-antigen, and the like), and thus is affected with such a disease or condition.

Screening for Agents that Modulate Antigen-Specific CTL-APC Interactions

The present invention further provides methods of identifying agents that modulate (i.e., "increase" or "decrease", or "enhance" or "inhibit", respectively) antigen-specific CTL-APC interactions, and thus modulates lysis of a target cell. The methods generally involve contacting the target APCs, or the CTLs, with a candidate agent prior to or during incubation of the CTLs with the target APCs, and detecting the effect of the candidate agent upon induction of CTL-mediated apoptosis of the target APC.

A reduction in fluorescence in the target APC as a result of CTL interaction, compared to in the absence of the agent (e.g., in a control sample), indicates that the agent inhibits antigen-specific cell lysis. Similarly, an increase in fluorescence in the target APC as a result of CTL interaction, compared to in the absence of the agent (e.g., in a control sample), indicates that the agent enhances antigen-specific cell lysis. Suitable control samples in such assays are those that do not contain the test agent. Suitable control samples in such assays are those that do not contain the test agent.

Agents of interest modulate antigen-specific CTL-target APC interactions such that there is an increase or decrease in signal relative (relative to in the absence of the agent) of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or more, when compared with a suitable control. Agents that increase CTL killing are of interest in applications such as treating cancer, treating intracellular pathogen infections, and the like. Agents that decrease CTL killing are of interest in application such as treating cell-mediated autoimmune diseases (e.g., graft-versus-host disease, and the like).

The terms "test agent," "candidate agent," "substance," and "compound" are used interchangeably herein. Candidate agents encompass numerous chemical classes, typically synthetic, semi-synthetic, or naturally-occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and typically include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Agents further encompass interfering RNA molecules, antibodies, and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidation, etc. to produce structural analogs.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components are added in any order that provides for the requisite binding. Incubations are performed at any suitable temperature, typically between 4.degree. C. and 40.degree. C. Incubation periods are selected for optimum activity, but may also be optimized to facilitate rapid high-throughput screening. Typically between 0.1 and 1 hour will be sufficient.

As is readily apparent, design of the assays described herein are subject to a great deal of variation, and many formats are known in the art. The above descriptions are merely provided as guidance and one of skill in the art can readily modify the described protocols, using techniques well known in the art.

Kits

Kits for use in connection with the subject invention are also provided. The above-described assay reagents, including, for example, arrays having bound cDNAs for array-based transfection of a desired target cell, target cells having a desired MHC phenotype, one or more fluorogenic caspase substrates, and the like, can be provided in kits, with suitable instructions and other necessary reagents, in order to conduct the assays as described above. Instructions (e.g., written, tape, VCR, CD-ROM, etc.) for carrying out the assay usually will be included in the kit. The kit can also contain, depending on the particular assay used, other packaged reagents and materials (i.e. wash buffers and the like). Standard assays, such as those described above, can be conducted using these kits.

The instructions are generally recorded on a suitable recording medium. For example, the instructions may be printed on a substrate, such as paper or plastic, etc. As such, the instructions may be present in the kits as a package insert, in the labeling of the container of the kit or components thereof (e.g., associated with the packaging or sub-packaging), etc. In other embodiments, the instructions are present as an electronic storage data file present on a suitable computer readable storage medium, e.g., CD-ROM, diskette, etc, including the same medium on which the program is presented.

In yet other embodiments, the instructions are not themselves present in the kit, but means for obtaining the instructions from a remote source, e.g. via the Internet, are provided. An example of this embodiment is a kit that includes a web address where the instructions can be viewed from or from where the instructions can be downloaded.

Still further, the kit may be one in which the instructions are obtained are downloaded from a remote source, as in the Internet or world wide web. Some form of access security or identification protocol may be used to limit access to those entitled to use the subject invention. As with the instructions, the means for obtaining the instructions and/or programming is generally recorded on a suitable recording medium.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

The following method and material were used in the Example(s) below.

Mice and cell culture. Experiments utilizing mice, 6 to 8 week old C57BL/6N (B6) strain (Charles River), were approved and followed regulations of the Health Sciences Animal Policy and Welfare Committee, Faculty of Medicine, University of Alberta. The human kidney embryonic cell line 293T (GenHunter Corporation) was grown in DMEM supplemented with 10% FCS, 100 μg/ml streptomycin, 100 IU/ml penicillin and 2 mM glutamine. Murine HY Uty-specific T cell clone CTL-10 (Greenfield, A. et al. *Nat. Genet.* 14, 474-478 (1996), was restimulated weekly with $5\times10^6$ irradiated male C57BL/6N mouse splenocytes in DMEM supplemented with 10% FCS, $5\times10^{-5}$ M 2-mercaptoethanol, 0.56 mM L-arginine, 6 μg/ml folic acid, 36 mg/ml L-asparagine, 1 mM sodium pyruvate, 1.4 mM L-glutamine, 0.5 mg/ml gentamycin and 40 IU/ml rIL-2.

Engineering of target APC. Full-length cDNA sequences encoding $D^b$ and B7.1 were inserted into the same mammalian expression vector pBudCE4.1 (Invitrogen), which allowed expression of two heterologous genes through a single transfection. Trypsinized 293T cells ($1\times10^7$) were resuspended in serum-free DMEM containing 20 μg of purified pBudCE4.1-$D^b$-B7.1 plasmid DNA, incubated on ice for 15 minutes, and electroporated using a BTX ECM830 electroporator (Harvard Apparatus) at 300 V with three 5 milli-second pulses. After culture for 3 weeks with 200 μg/ml of zeocin (Invitrogen), zeocin-resistant transfectants were stained with FITC-conjugated $D^b$ and phycoerythrin (PE)-conjugated mouse B7-1 specific mAbs (eBiosciences), and sorted by a FACSVantage cytometer (BD Biosciences). Stable transfectants expressing $D^b$ and B7.1 were further selected by limiting dilution and maintained in 100 μg/ml of zeocin.

cDNA plasmid spotting. To prepare a HY minigene expression DNA construct, two synthetic complementary oligonucleotides encoding HY peptide, $Uty_{246-254}$, MWMHHNMDLI (SEQ ID NO: 1), sense, 5'-GGCCGCCATGTGGATGCACCATAATATGGATCTAAT-3' (SEQ ID NO: 2), and antisense, 5'-CTAGATTAGATCCATATTATGGTGCATCCACATGGC-3' (SEQ ID NO: 3), were annealed together, and subsequently inserted into the pcDNA3/neo vector (Invitrogen, Carlsbad, Calif., USA) using Not I and Xba I restriction sites. To generate the EGFP-HY minigene construct, sense 5'-GATCCCAACACTTAGGTTGGATGCACCATAATATGGATCTAATTTGAT-3' (SEQ ID NO: 4) and antisense 5'-CTAGATCAAATTAGATCCATATTATGGTGCATCCAACCTAACTGTTGG-3' (SEQ ID NO: 5) oligonucleotides were annealed together, and subsequently inserted into the pEGFP-C1 vector (Clontech) using EcoR I and Xba I restriction sites. After transformation of *E. coli* DH5a cells, plasmid DNA was purified using an Endofree plasmid preparation kit (Qiagen).

Lipid-DNA complexes. Lipid-DNA complexes were prepared using Effectene transfection Kit (QIAGEN) by a procedure modified from Ziauddin et al (Ziauddin, J. & Sabatini, D. M. Nature 411, 107-110 (2001)) Briefly, after 3.2 μg DNA was diluted with 30 μl of DNA condensation Buffer EC containing 0.4 M sucrose, then 13.5 μl of Enhancer solution was added and mixed. Following a 5 minute incubation at room temperature, 20 μl Effectene transfection reagent was added and mixed with gentle vortexing. The mixture was at room temperature for 10 minutes, then a ⅓ volume of 0.2% gelatin was added. After mixing, 20 μl of the solution was transferred into 96-well polypropylene library storage plates (BD Biosciences), for printing on functionalized epoxy microarray slides (TeleChem International), using a manual MicroCaster arrayer equipped with 8 pins (Schleicher & Schuell Bioscience). Individual pins transferred a small volume of the 'lipid-DNA' solution to the slide while touching the slide surface for 200-500 ms. Printed slides were stored at room temperature or 4° C. in a vacuum desiccator.

Reverse transfection. Air-dried DNA-liposome slides were attached to a plastic chamber from the Lab-Tek chambered slide system (Nalge Nunc International), and placed in a QuadriPerm 4-compartment cell culture dish (Sigma). Healthy 293T cells were harvested by trypsinization and re-suspended in complete DMEM medium at a density of $0.5\times10^6$ cells/ml and 5 ml of cell suspension was transferred onto the chambered slide. Cells were cultured in a 5% $CO_2$ humidified incubator at 37° C. for 24-48 h. Slides were washed twice with ice-cold PBS, fixed with 3.7% paraformaldehyde in PBS at room temperature for 20 min, and fluorescence images were acquired using a Typhoon 8400 scanner (Amersham Pharmacia) or ScanArray Express HT scanner (Perkin Elmer).

Assay of CTL activity on microarray. Antigen specific CTL in complete growth medium, $3.0\times10^6$ cells/ml in 2 mls, were routinely transferred onto the engineered APC monolayer on microarray. Fourteen μl of a 150×SR-VAD-FMK (BIOMOL) stock solution was added to the medium. After brief mixing, slides were incubated at 37° C. for 4 hours. Slides were washed twice with 1× Wash Buffer from the multi-caspase detection kit (BIOMOL), incubated with 3.7% paraformaldehyde in PBS at room temperature for 20 min, and washed twice with PBS to remove excess fixative. Fluorescence images were acquired using Typhoon 8400 or ScanArray Express HT fluorescence scanners.

Transient transfection. Oligonucleotides encoding HY peptide, MWMHHNMDLI (SEQ ID NO: 1) and QQLGWMHHNMDLI (SEQ ID NO: 6), were synthesized by Sigma-Genosys. Influenza A virus nucleoprotein (NP) cDNA in expression vector was provided by Dr. J. Yewdell (NIH). Engineered 293T cells stably expressing $D^b$ and B7.1 were transiently transfected with plasmid DNA constructs encoding the HY minigene or its EGFP fusion using Effectene. The APCs transfected with pcDNA3 vector only, pcDNA3-NP, or pEGFP-C1 served as controls.

$^{51}$Cr release assay. Following transient transfection with plasmid DNA containing HY mini-gene, NP cDNA inserts or vector alone, engineered APCs ($0.5\times10^6$) were labeled with 100 μl $^{51}$Cr at 37° C. for 2 h, washed twice, dispensed into triplicate cultures at $5\times10^3$ target cells/well in 96-well round-bottom microtiter plates (Corning), and incubated for 4 h with effector T cells ($2.5\times10^4$ cells/well) in a volume of 200 μl. Radioactivity was determined using a Wallac MicroBeta Scintillation/Luminescence Counter (PerkinElmer). Specific lysis was calculated with the following formula: (experimental release−spontaneous release)/(maximal release−spontaneous release)×100. Spontaneous release was determined from $^{51}$Cr-labeled target cells incubated in the presence of medium only, and maximal release in the presence of 5% Triton X-100 without CTL.

Flow cytometric cytotoxicity assay. Following transient transfection with plasmid DNA containing the HY minigene, NP cDNA inserts or vector alone, $0.5\times10^6$ engineered APCs were incubated with CellTracker Orange dye (Molecular Probes) for 30 min at room temperature and recovered for 1 h at 37° C. Labeled APCs were then incubated for 3 h with $2.5\times10^6$ of effector T cells in a volume of 300 μl. Samples were washed twice with PBS, and re-suspended in 300 μl of PBS containing 10 μM SR-VAD-FMK. Cell suspensions were incubated at 37° C. for another hour, washed twice and analyzed in a FACSCalibur cytometer with CellQuest software (BD Biosciences).

Example 1

Recombinant Target APCs

Target APCs were engineered from human 293T cells by modifying the 293T cells to stably express mouse MHC class I molecule, H-2D$^b$ to present an antigen of interest, as well as a costimulatory ligand B7.1. The mouse CTL clone 10 recognized an HY male minor hostocompatability antigen peptide, Uty$_{246-254}$ WMHHNMDLI (SEQ ID NO: 7), bound to H-2D$^b$. Engineered 293T cells transiently transfected with a mini-gene encoding the HY peptide epitope were lysed by CTL-10, as detected in $^{51}$Cr-release assay and target cell FLICA retention, confirming the specificity of response to the APC and utility of FLICA.

Example 2

Detection of Antigen-Specific CTL Cytotoxicity

Figure 2:
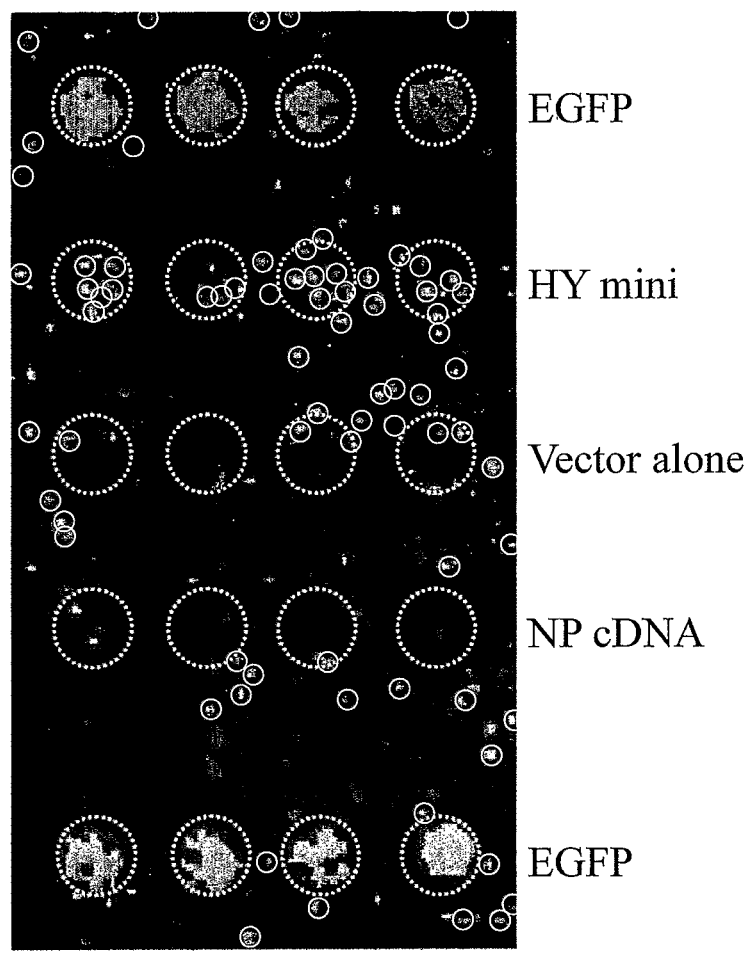
FIG. 2 shows detection of antigen specific CTL response to reverse transfected APC on microarray. 293T APC expressing $D^b$ and B7.1 were reverse-transfected with pcDNA3 vector alone, or vector encoding EGFP, NP or HY peptide. Dashed circles delineate features on the array containing recombinant target APCs. Open circles represent "red" signal associated with FLICA binding. All other light-colored images on the dark background of the array represent green fluorescent signal indicative of EGFP expression. Imaging of EGFP expression (top panel, "green") and FLICA binding (center panel, "red") was obtained by fluorescence scanning at 50 μm resolution.

Expression of individual cDNAs at defined addresses on microarray was combined with antigen specific CTL recognition by FLICA retention and localization. Vectors containing EGFP, influenza nucleoprotein (NP) HY mini-gene cDNAs, or vector alone, as lipid-DNA complexes in gelatin were deposited on microarray slides. Gelatin preserved the location of deposited lipid-DNA complexes on the microarray. The 293T cells expressing mouse H-2 D$^b$ and B7.1 were applied to each slide. After 32 hours, HY-specific CTL-10 was added, and fluorescence images of the slides were obtained after 4 hours. Intense green fluorescence at GFP control vector spots indicated successful transient transfection of APC (FIG. 2). Importantly, a strong concentration of FLICA was observed, indicated as red fluorescence, where the antigen-encoding HY mini-gene was spotted, but little or no FLICA where the NP or vector alone was spotted (FIG. 2). These data indicated for the first time that antigen specific CTL-mediated cytotoxicity was detectable on a reverse transfected microarray.

Example 3

Figure 3:
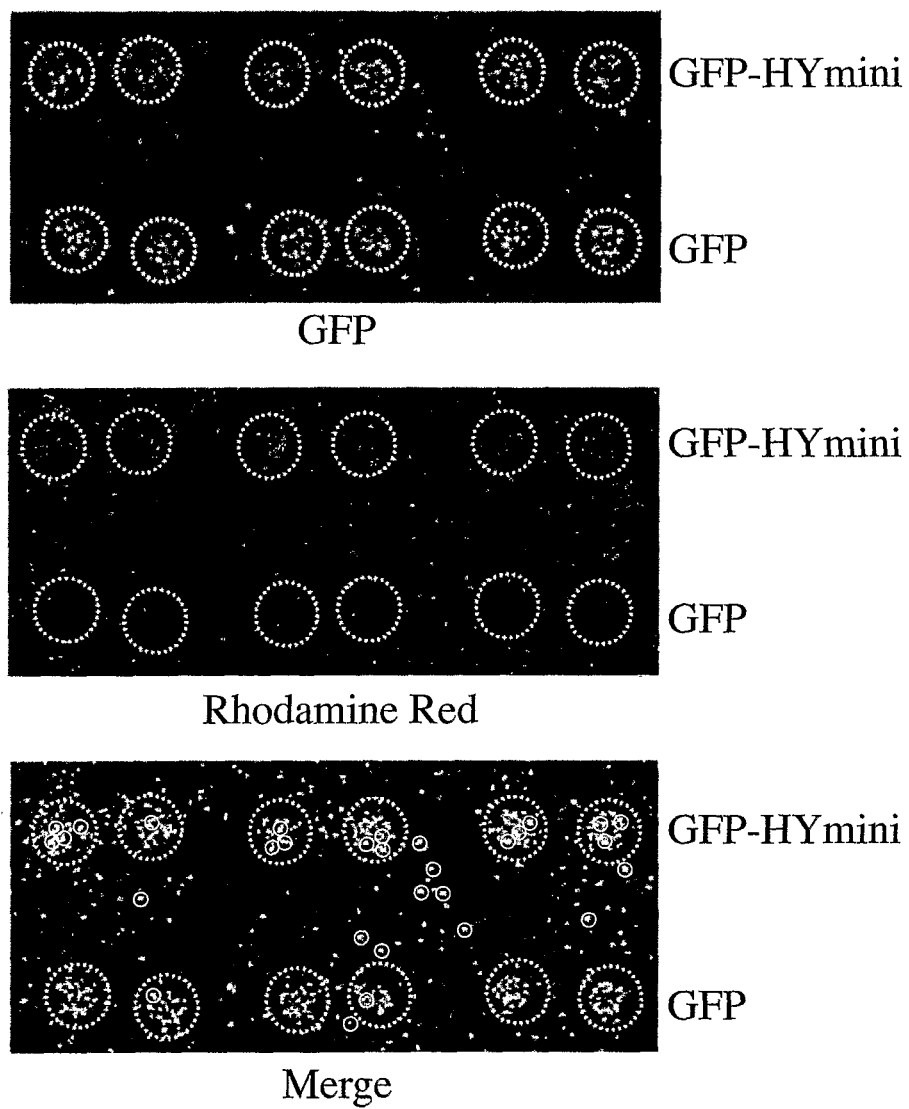
FIG. 3. Processing of a GFP fusion protein detected by antigen specific CTL response on microarray. 293T APC expressing Db and B7.1 were reverse-transfected with pcDNA3 vector encoding EGFP or an EGFP-HY peptide fusion protein and apoptosis of APC induced by HY-specific CTL was detected by FLICA binding. Dashed circles delineate features on the array containing recombinant target APCs. Light-colored images on the dark background of the array represent green fluorescent signal in the top panel and red fluorescent signal in the center panels. Open circles in the bottom panel represent "yellow" signal where the "red" and "green" signals colocalize, which indicates colocalization of GFP expression and FLICA binding (caspase activity indicative of CTL killing). The Images were obtained by fluorescence scanning at 5 micron resolution; EGFP expression ("green") and FLICA binding ("red"). Bottom panel is a merged image of the upper panels.

Detection of Antigen from a Processed Polypeptide in Recombinant Target APCs at the Single-Cell Level A DNA construct encoding the HY peptide, Uty$_{242-254}$ QQLGWMHHNMDLI (SEQ ID NO: 6) fused to EGFP (GFP-HYmini) was prepared. Expression of the GFP-HY fusion protein was comparable to GFP by reverse transfection on the microarray (FIG. 3, upper panel). Processing of the GFP-HY fusion protein to yield the HY peptide by the APC was detected as CTL-induced concentration of FLICA (red) where the GFP-HYmini, but not GFP vector was spotted (FIG. 3, middle panel). A merged image indicated that a significant fraction of cells expressing the GFP-HY fusion protein are also FLICA positive and appear yellow, while such is not the case for GFP-expressing cells (FIG. 3, bottom panel). These results demonstrated that the CTL microarray assay detected processing and presentation of a peptide epitope generated from a longer protein precursor. In addition, at 5 µm resolution, the observed CTL recognition of APC is likely at the single cell level on the microarray, providing a better opportunity to identify antigens when CTLs are at low frequency.

It is evident from the above results and discussion that the subject invention provides an important new means for the detection of antigen-specific CTLs and for identification of antigens recognized by antigen-specific CTLs. As such, the subject methods and systems find use in a variety of different applications, including research, medical, therapeutic, and other applications. Accordingly, the present invention represents a significant contribution to the field.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for identifying a cytolytic T lymphocyte (CTL) antigen, the method comprising:

contacting a sample comprising a cytolytic T lymphocyte (CTL) with an array comprising a plurality of adherent recombinant antigen-presenting cells (APCs) adhered to a surface of the array at different, discrete locations on the array, wherein the adherent recombinant APCs express different recombinant polynucleotides encoding different polypeptides, and wherein the different, discrete locations on the array correlate with the different recombinant polynucleotides expressed by the adherent recombinant APCs;

washing the array; and detecting the presence or absence of caspase activity in the plurality of adherent recombinant APCs by detecting the presence of a fluorescent signal generated from a fluorogenic caspase substrate present in said adherent recombinant APCs;

wherein the presence of a fluorescent signal in an adherent recombinant APC is indicative of an antigen-specific interaction between the CTL and the adherent recombinant APC and indicates the recombinant polynucleotide of the adherent recombinant APC encodes a polypeptide that comprises a CTL antigen.

2. The method of claim 1, wherein the recombinant polynucleotides encode a tumor antigen.

3. The method of claim 1, wherein the recombinant polynucleotides encode an antigen of an intracellular pathogen.

4. The method of claim 3, wherein the antigen is a viral antigen, bacterial antigen, antigen of a parasite, or fungal antigen.

5. The method of claim 1, wherein the recombinant polynucleotides encode an autoantigen.

6. The method of claim 1, wherein the fluorogenic caspase substrate is a fluorogenic multi-caspase substrate.

7. The method of claim 1, wherein the CTL is in a biological sample obtained from a subject.

8. The method of claim 1, wherein the CTL is a CTL clone.

9. The method of claim 1, wherein said contacting is for about 1 to 4 hours.

10. The method of claim 1, wherein said contacting is for about 1 hour.

11. The method of claim 1, wherein the adherent recombinant APCs were produced by plating the APCs onto an array surface comprising the recombinant polynucleotides deposited on an array location, wherein said plating is under appropriate conditions for adherence of the APCs to the array surface and introduction of the recombinant polynucleotide into the adherent APC, and wherein the array location at which the recombinant polynucleotide was deposited corresponds to the location of the adherent APC containing the recombinant polynucleotide.

12. The method of claim 1, wherein the adherent recombinant APC contains a recombinant polynucleotide encoding a polypeptide fragment.

13. The method of claim 12, wherein the polypeptide fragment provides a T cell antigen that is presented in Class I MHC for recognition by a CTL specific for that antigen.

* * * * *